(12) United States Patent
Askill

(10) Patent No.: US 7,354,889 B2
(45) Date of Patent: Apr. 8, 2008

(54) METHOD OF REMOVING MEDICAL ADHESIVE WITH A REMOVER COMPRISING TETRAHYDROFURFURYL ACETATE

(75) Inventor: Ian Nigel Askill, Colorado Springs, CO (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 385 days.

(21) Appl. No.: 11/216,701

(22) Filed: Aug. 31, 2005

(65) Prior Publication Data

US 2007/0054821 A1 Mar. 8, 2007

(51) Int. Cl.
*C11D 3/43* (2006.01)
(52) U.S. Cl. .................. 510/134; 510/432; 156/344
(58) Field of Classification Search ............. 510/134, 510/432; 156/344
See application file for complete search history.

(56) References Cited

U.S. PATENT DOCUMENTS

| | | | |
|---|---|---|---|
| 4,659,609 A | 4/1987 | Lamers et al. | |
| 4,775,582 A | 10/1988 | Abba et al. | |
| 4,833,003 A | 5/1989 | Win et al. | |
| 4,853,281 A | 8/1989 | Win et al. | |
| 5,128,057 A * | 7/1992 | Bixenman et al. | 510/175 |
| 6,696,517 B2 * | 2/2004 | Löffler et al. | 524/555 |
| 2003/0060380 A1 | 3/2003 | Ayarza et al. | |
| 2005/0245407 A1* | 11/2005 | Ishihara et al. | 510/101 |
| 2006/0223878 A1* | 10/2006 | Scialdone | 514/427 |

\* cited by examiner

*Primary Examiner*—Charles Boyer
(74) *Attorney, Agent, or Firm*—James B. Robinson

(57) ABSTRACT

Medical adhesive may be removed by applying a solution including tetrahydrofurfuryl acetate (THFA) to the surface upon which is located the adhesive and rubbing the surface to facilitate removal of the adhesive. The solution may be applied to a wipe before application to the surface and the wipe may be used to rub the surface. The surface may be living or dead human or animal skin, hard surfaces and medical instruments. Various additional ingredients may be added to the solution, like perfumes, emollients and other commonly known skin products and polymer diluents.

15 Claims, No Drawings

METHOD OF REMOVING MEDICAL ADHESIVE WITH A REMOVER COMPRISING TETRAHYDROFURFURYL ACETATE

The present invention relates generally to the removal of medical adhesives from mammalian tissues such as hair and skin.

Medical adhesives have many uses, including securing wound dressings, surgical drapes, tapes, sensors and the like, as well as skin sealant and liquid sutures etc.

Medical adhesives in the form of surgical skin sealant are applied to the skin prior to, for example, surgery, in order to reduce the risk of infection by gluing in place any microbes, germs, dead skin and the like, so that they cannot move into the surgical site.

Medical adhesives may also be used to hold together the sides of a wound or surgical incision to encourage healing, much like a butterfly bandage or stitches might do.

The medical adhesive is normally allowed to slough off the skin naturally with time. It may be removed from the skin, however, in the case of surgery for example, when the surgery is completed. Acetone is currently used to remove medical adhesives but is somewhat limited in applicability, especially in a surgical environment, because of concerns about flammability and irritation of the skin. Mineral oil and soap and water are also used but suffer from a lack of efficacy.

Removers for the adhesive should be able to remove the adhesive without damaging the skin, without strong smells, and without being flammable.

SUMMARY

The present invention provides a method for removing medical adhesive from surfaces safely and effectively. Medical adhesive may be removed by applying a solution including tetrahydrofurfuryl acetate (THFA) to the surface upon which is located the adhesive and rubbing the surface to facilitate removal of the adhesive. The solution may be applied to a wipe before application to the surface and the wipe may be used to rub the surface. The surface may be living or dead human or animal skin, hair, organs and other tissues, hard surfaces and medical instruments. Various additional ingredients may be added to the solution, like perfumes, emollients and other commonly known skin products.

DETAILED DESCRIPTION

Medical adhesives are often used in surgical environments to reduce the possibility that extraneous materials will enter the incision site. Loose skin cells and other potential contaminates on the skin can be immobilized by the application of an adhesive that coats the skin and thus holds these materials in place.

Medical adhesives may also be used to aid in wound closure by holding together opposite sides of a wound or incision site and so allowing the skin to heal more quickly than it would without the adhesive.

In the case of surgical applications of medical adhesives, once the surgery is complete it may be desired to remove the adhesive. Acetone is often chosen for adhesive removal but is flammable, irritates the skin, and has an unpleasant odor.

The inventor has found that tetrahydrofurfuryl acetate (THFA) can dissolve medical adhesive common in the surgical suite. The inventor has further found that diluents like perfumes, emollients and other additives common to skin products, and diluents common to plastics and adhesives technology may be added in an amount up to about 20 weight percent without significantly interfering with the solvent properties of the THFA. Potential diluents include, but are not limited to, vegetable oils like, for example soy oil, corn oil and safflower oil, vitamin E, citrates, and phthalate plasticizers, fatty acid esters, triacetin and the like.

The THFA solution may be applied to the skin by the use of wipers or by direct application to the skin in liquid form followed by rubbing or abrasion by a wiper. The THFA solution may be sterile or non-sterile and can have a range of coverage areas depending on the amount of solution and abrasiveness of the wiper. Wipers that may be used in conjunction with the THFA solution include, but are not limited to, those taught in U.S. Pat. Nos. 4,659,609, 4,775,582, 4,833,003 and 4,853,281.

The method of using the THFA solution includes the steps of providing the solution and adhesive coated surface to which the solution will be applied, applying the solution to the surface, and rubbing or abrading the surface to facilitate the removal of the adhesive. As noted above, the THFA may be applied to a wiper before application to the surface and the wiper may be used to rub the surface.

Also provided is system for teaching a method of using an adhesive remover having the steps of providing a container within which is the remover, labeling the container with steps for using the remover where the steps are; applying the remover to a surface and rubbing the remover on the surface in order to enhance removal.

A composition for removing adhesive is also provided where the composition includes tetrahydrofurfuryl acetate and ingredients such as perfumes, emollients, dyes, colorants, vegetable oils, vitamin E, citrates, phthalate plasticizers, fatty acid esters, triacetin and mixtures thereof.

It should be noted that the remover may be used on any surface on which is located a medical adhesive. Thus the remover may be used to remove adhesive from living or dead human or animal skin, hair, organs and other tissues, hard surfaces, e.g. countertops, upon which adhesive may have been inadvertently applied, or from medical instruments, for example.

Tetrahydrofurfuryl acetate has a CAS registry number of 637-64-9. It has a molecular formula of $C_7H_{12}O_3$, a weight of 144.17, and a boiling point of about 194° C. at 753 mmHg. Synonyms for THFA include tetrahydro-2-furyl methyl acetate, 2-(acetoxymethyl) tetrahydrofuran, 2-acetoxymethyl oxolane and tetrahydro-2-furan methanol acetate. THFA is non-flammable and is used currently as a flavoring or perfume ingredient.

Exemplary solutions of THFA include:
a. 100% THFA which rapidly removes polyoctyl cyanoacrylate from skin after application of BAND-AID™ Liquid Bandage, Skin Crack Gel, (Johnson &Johnson Skillman, N.J.) However the skin after removal appears slightly white and dusty and may have been de-fatted.
b. 80% THFA, 20% triacetin, which readily removes polybutyl cyanoacrylate from skin after application of Nexcare™ Liquid Bandage (3M Consumer Health Care, St Paul, Minn.)
c. 90% THFA, 9% safflower oil and 1% vitamin E, which readily removes adhesive residue from IoBan™ antimicrobial surgical drape (3M Healthcare, St Paul Minn.)

It should be appreciated by those skilled in the art that various modifications and variations can be made to the embodiments of the present invention described and illustrated herein without departing from the scope and spirit of the invention. The invention includes such modifications and variations coming within the meaning and range of equivalency of the appended claims.

What is claimed is:

1. A method of removing adhesive from a surface comprising the steps of:
    providing a surface upon which is an adhesive;
    providing an adhesive remover;
    applying said remover to the surface;
    rubbing the remover on the surface in order to enhance removal;
    wherein said remover comprises tetrahydrofurfuryl acetate.

2. The method of claims 1 wherein said surface is skin.

3. The method of claim 2 wherein said skin is living human skin.

4. The method of claim 2 wherein said skin is dead human skin.

5. The method of claim 2 wherein said skin is animal skin.

6. The method of claim 1 wherein said surface is tissue.

7. The method of claim 1 wherein said remover further comprises ingredients selected from the group consisting of perfumes, emollients, dyes, colorants, vegetable oils, vitamin E, citrates, phthalate plasticizers, fatty acid esters, triacetin and mixtures thereof.

8. A method of removing adhesive from a surface comprising the steps of:
    providing a surface upon which is an adhesive;
    providing an adhesive remover;
    applying said remover to a wipe;
    rubbing said wipe on the surface in order to enhance removal;
    wherein said remover comprises tetrahydrofurfuryl acetate.

9. The method of claim 8 wherein said surface is skin.

10. The method of claim 9 wherein said skin is living human skin.

11. The method of claim 8 wherein said skin is dead human skin.

12. The method of claim 8 wherein said skin is animal skin.

13. The method of claim 8 wherein said surface is tissue.

14. The method of claim 8 wherein said remover further comprises ingredients selected from the group consisting of perfumes, emollients, dyes, colorants, vegetable oils, vitamin E, citrates, phthalate plasticizers, fatty acid esters, triacetin and mixtures thereof.

15. The method of claim 1 wherein the adhesive remover is housed within a container, which is labeled with steps for using said remover comprising:
    applying said remover to a surface; and
    rubbing the remover on the surface in order to enhance removal.

* * * * *